United States Patent [19]

Barton et al.

[11] 4,401,596
[45] Aug. 30, 1983

[54] NOVEL 17-OXAZOLINE-STEROIDS

[75] Inventors: Derek H. Barton; William B. Motherwell; Samir Zard Zard, all of Gif-sur-Yvette, France

[73] Assignee: Roussel Uclaf, Paris, France

[21] Appl. No.: 317,584

[22] Filed: Nov. 3, 1981

[30] Foreign Application Priority Data

Nov. 5, 1980 [FR] France ............................ 80 23575

[51] Int. Cl.³ .............................................. C07J 71/00
[52] U.S. Cl. ............................................... 260/239.55
[58] Field of Search ........................ 260/239.55, 239.5

[56] References Cited

U.S. PATENT DOCUMENTS 4,218,446 8/1980 Solyom et al. .................. 260/239.5
4,232,013 11/1980 Palladino et al. ............... 260/239.5

Primary Examiner—Elbert L. Roberts

[57] ABSTRACT

Novel 17-oxazoline-steroids of the formula

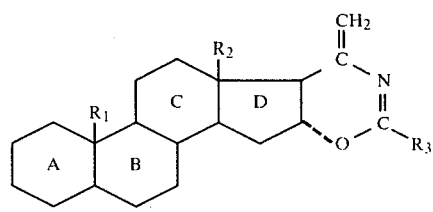

wherein $R_1$ is selected from the group consisting of hydrogen, alkyl of 1 to 4 carbon atoms optionally substituted with a member of the group consisting of halogen, oxygen function and nitrogen function and alkenyl and alkynyl of 2 to 4 carbon atoms, $R_2$ is alkyl of 1 to 4 carbon atoms, $R_3$ is selected from the group consisting of hydrogen and hydrocarbon of 1 to 8 carbon atoms and the A,B,C and D rings optionally contain at least one double bond and are optionally substituted with at least one member of the group consisting of —OH, $=$O, halogen, alkyl and alkoxy of 1 to 4 carbon atoms, and alkenyl and alkynyl of 2 to 4 carbon atoms which are useful intermediates for known steroids having in the 17-position the

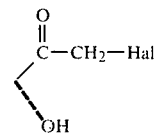

group.

4 Claims, No Drawings

NOVEL 17-OXAZOLINE-STEROIDS

STATE OF THE ART

Raggio et al [J. Org. Chem., Vol. 41, No. 10 (1976), p. 1873-75] describe the preparation of progesterone from dehydro epiandrosterone which includes the reaction of the 17-keto-androstane compound with 2-(diethyl-phosphono)-propionitrile. Lefwick [Tetrahedron, Vol. 26, No. 2 (1970), p. 321-329] describes steroidal oxazolidones and U.S. Pat. No. 3,338,892 is also related.

OBJECTS OF THE INVENTION

It is an object of the invention to provide the novel 17-oxazoline steroids of formula I and a novel method for their preparation.

It is a further object of the invention to provide a novel process for the preparation of steroids having in the 17-position the

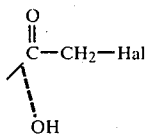

group.

These and other objects and advantages of the invention will become obvious from the following detailed description.

THE INVENTION

The novel compounds of the invention are 17-oxazolinesteroids of the formula

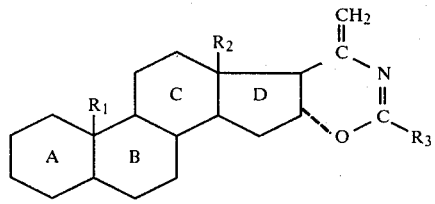

wherein $R_1$ is selected from the group consisting of hydrogen, alkyl of 1 to 4 carbon atoms optionally substituted with a member of the group consisting of halogen, oxygen function and nitrogen function and alkenyl and alkynyl of 2 to 4 carbon atoms, $R_2$ is alkyl of 1 to 4 carbon atoms, $R_3$ is selected from the group consisting of hydrogen and hydrocarbon of 1 to 8 carbon atoms and the A,B,C and D rings optionally contain at least one double bond and are optionally substituted with at least one member of the group consisting of —OH, =O, halogen, alkyl and alkoxy of 1 to 4 carbon atoms, and alkenyl and alkynyl of 2 to 4 carbon atoms.

Examples of $R_1$ are alkyl such as methyl or ethyl; alkyl substituted with an oxygen function such as hydroxy methyl, hydroxy ethyl, formyl and acetyl; alkyl substituted with a nitrogen function such as amino methyl and amino ethyl; alkyl substituted with halogen such as a halomethyl like —CH$_2$Hal when Hal is chlorine, bromine or fluorine; alkenyl such as vinyl and allyl; alkynyl such as ethynyl.

Examples of $R_2$ are methyl and ethyl and examples of $R_3$ are hydrogen or hydrocarbons such as alkyl of 1 to 8 carbon atoms.

When the A,B,C and D rings contain one or more double bonds, the double bonds are preferably in the 1(2), 3(4), 4(5), or 9(11) positions or in a system of conjugated bonds in the 3(4) and 5(6) or 4(5) and 6(7) or 1(2) and 4(5) positions or an aromatic system of three double bonds in the 1,3 and 5 positions or a system of three double bonds in the 1(2), 4(5), 6(7) positions.

When the A,B,C, and D rings are substituted with a hydroxyl group, it is preferably in the 3- or 11-positions and keto substituents are preferably in the 3- or 11-position. Halogen substituents such as fluorine, chlorine or bromine are preferably in the 6- or 9α-positions and the preferred alkyl substituents are methyl or ethyl in the 2-,6-,7-, 16α- or 16β-positions and the preferred alkoxy substituents are methoxy or ethoxy in 3 or 11β-positions. The preferred alkenyl substituents are vinyl or allyl in the 11β-position and the preferred alkynyl substituent is 11β-ethynyl.

Preferred compounds of formula I are those wherein $R_2$ is methyl and those wherein $R_1$ is hydrogen or methyl and those wherein $R_3$ is hydrogen and those wherein $R_3$ is alkyl of 1 to 4 carbon atoms, especially methyl.

Particularly preferred compounds of the invention are those of the formula

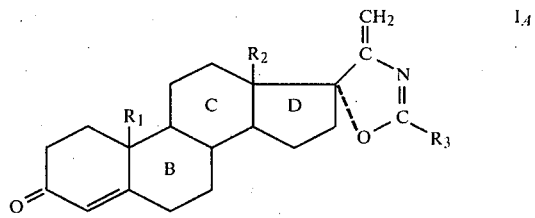

wherein $R_1$, $R_2$ and $R_3$ have the above definitions and the B, C and D rings may contain at least one double bond and may be optionally substituted as discussed supra and those of the formula

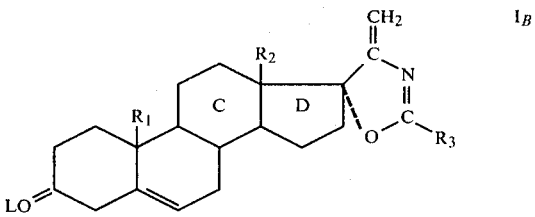

wherein $R_1$, $R_2$ and $R_3$ have the above definition, L is an alcohol protective group and C and D may contain at least one double bond and may be substituted as discussed supra.

Examples of suitable alcohol protective groups are methoxymethyl, β-methoxyethoxymethyl, benzyl, p-nitrobenzyl, trimethylsilyl, tert.-butyldimethylsilyl, triethylsilyl, acetyl, propionyl and benzoyl.

Especially preferred compounds of the invention are those of formula $I_A$ wherein the B,C and D rings do not contain any unsaturation and those of formula $I_B$ wherein the C and D rings do not contain any unsaturation. An especially preferred compound is (17 R) 4'-methylenespiro-[Δ$^4$-androstene-17,5'-(4'H)-oxazol]-3-one.

The novel process of the invention for the preparation of a compound of formula I comprises reacting a compound of the formula

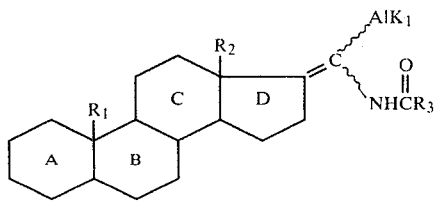

wherein the $$-NH\overset{O}{\overset{\|}{C}}R_3$$

group is in the cis and/or trans positions $R_1$, $R_2$, $R_3$, A, B, C and D have the above definitions and $AlK_1$ is alkyl of 1 to 8 carbon atoms with an epoxidation agent and then reacting the epoxidized compound simultaneously with an acid agent and a dehydration agent in an anhydrous medium to obtain the corresponding compound of formula I.

In a preferred mode of the process of the invention, the epoxidation agent may be a per acid such as m-chloroperbenzoic acid, perphthalic acid, peracetic acid or performic acid. The acid agent may be m-chlorobenzoic acid, phthalic acid, acetic acid or formic acid resulting from the epoxidation and the dehydration in the anhydrous medium is effected by reflux in toluene or benzene while azeotropically distilling the water of reaction. The preferred starting compound is N-($\Delta^{4,17(20)}$-pregnadiene-3-one-20-yl)-formamide which is used to prepare the compound of Example 2.

The starting compounds of formula II wherein $R_3$ is a hydrocarbon may be prepared by the process described by Barton et al [J. Chem. Soc. Perkin trans Vol. 1 (1975), p. 1242]. The compounds of formula II wherein $R_3$ is hydrogen may be prepared by reacting a compound of the formula

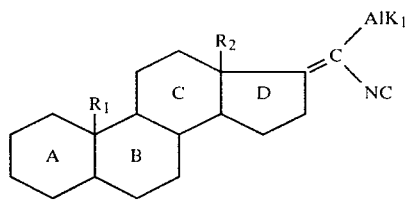

with a hydration agent in an acid medium for the isocyano group such as acetic acid, propionic acid, chloroacetic acid, oxalic acid or formic acid.

The compounds of formula V may be prepared by reacting a compound of the formula

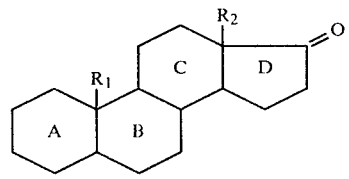

wherein $R_1$, $R_2$, A, B, C and D have the above definition with a compound of the formula

wherein $AlK_1$ has the above definition and $AlK_2$ is alkyl of 1 to 8 carbon atoms. In Example 2, 20-isocyano-3-methoxy-$\Delta^{3,5,17(20)}$-pregnatriene is prepared.

The invention also is directed to a process for the preparation of compounds of the formula

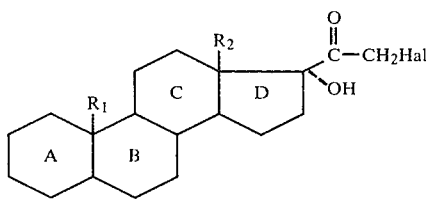

wherein $R_1$, $R_2$, A, B, C and D have the above definitions and Hal is a halogen starting from the compounds of formula I by a simple and rapid process with good yields. The compounds of formula IV are known steroids of great industrial interest. The process is especially useful to prepare the compounds described in French Pat. No. 1,048,609 and U.S. Pat. No. 3,646,012.

The compounds of the invention are very easily prepared from the corresponding 17-keto steroids and are equally very easily transformed into very important industrial products in the synthesis of cortisonic derivatives which have a very great commercial interest.

The process of the invention to prepare a compound of formula IV comprises reacting a compound of formula I with a basic agent and then a halogenation agent capable of introducing a halogen atom and then with a hydrolysis agent to obtain a compound of the formula

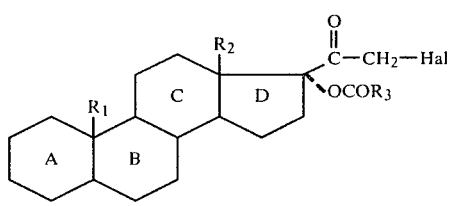

wherein $R_1$, $R_2$, $R_3$, A, B, C, D and Hal have the above definitions and reacting the latter with a saponification agent to obtain a compound of formula IV.

In a preferred mode of the process, the basic agent is a tertiary amine such as pyridine, the halogenation agent capable of introducing bromine is pyridinium perbromide [PyH+Br$_3^-$], the hydrolysis agent is a weak acid such as acetic acid or formic acid and the saponification agent is a base such as sodium hydroxide, potassium hydroxide or potassium bicarbonate.

In a particularly preferred mode of the latter process, (17R) 4'-methylenespiro-[$\Delta^4$-androstene-17,5'-(4'H)-oxazol]-3-one is reacted with a basic agent, then with an agent capable of introducing bromine, then with a hydrolysis agent and finally with a saponification agent to obtain 21-bromo-$\Delta^4$-pregnene-17α-ol-3,20-dione which is described in French Pat. No. 1,048,609 as an intermediate for the preparation of valuable therapeutic products.

In the following examples there are described several preferred embodiments to illustrate the invention. However, it is to be understood that the invention is not intended to be limited to the specific embodiments.

EXAMPLE 1

(17R) 3β-acetyloxy-2'-methyl-4'-methylene spiro [Δ$^5$-androsten-17,5'-(4'H) oxazole]

100 mg of m-chloroperbenzoic acid were added twice over a 20 minute interval to a solution of 300 mg of 3β-acetyloxy-20-acetylamino-Δ$^{5,17(20)}$-pregnadiene (prepared by process of Barton et al, J. Chem. Soc. Perkin 1/1975, p. 1242) in 50 ml of methylene chloride cooled in an ice bath and 20 minutes after the addition was complete, a few drops of dimethylsulfide were added thereto. The mixture was refluxed for 1½ to 2 hours and was then cooled. The reaction mixture was added with stirring to 50 ml of aqueous 5% sodium carbonate solution. The mixture was filtered and the product was dried to obtain 308 mg (50~60% yield) of (17R) 3β-acetyloxy-2'-methyl-4'-methylene spiro [Δ$^5$-androsten-17,5'-(4'H) oxazole] which after crystallization from methanol melted at 178°~180° C. and had a specific rotation of $[\alpha]_D^{20} = +92°$ (c=1% in chloroform).

NMR Spectrum (deuterochloroform):

Peaks at 5.25 ppm (hydrogen of 6-carbon-large doublet); at 4.90 ppm (hydrogen of 21-carbon-singulet); at 4.5-4.3 ppm (hydrogen of 3-carbon-large); at 4.25 ppm (hydrogen of 21-carbon-singulet); at 2.05 ppm (hydrogen of acetyloxy); at 1.95 ppm (hydrogens of

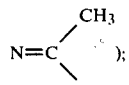

at 1.05 ppm (hydrogens of 19-CH$_3$-singulet); at 0.80 ppm (hydrogens of 18-CH$_3$).

EXAMPLE 2

(17R) 4'-methylene spiro-[Δ$^4$-androstene-17,5'-(4'H)-oxazol]-3-one

STEP A: Diethyl N-formylaminoethyl phosphonate

A mixture of 3.6 g of diethyl α-aminoethyl phosphonate [prepared by the process of Chalmers et al, J.A.C.S., Vol. 75 (1953), p. 5278] and 2 g of formylacetic anhydride stood overnight at room temperature and the mixture was heated at 120° C. at a pressure of 0.5 to 1 mm Hg for 15 to 20 minutes. The residue was used as is for the next step but distillation thereof led to pure diethyl N-formylamino ethyl phosphonate with a boiling point of 148°~150° C. at 0.5 mm Hg.

NMR Spectrum (deuterochloroform):

Peaks at 8.15 ppm (large singulet-hydrogen of

at 7.80 ppm (hydrogen of —NH—); at 1.1–1.6 ppm (hydrogens of CH$_3$).

STEP B: Diethyl 1-isocyanoethylphosphonate

A solution of 5.5 g of phosgene in 40 ml of dichloromethane was added over 30 minutes at 35° to 40° C. to a mixture of 9.85 g of Step A, 16 ml of triethylamine and 25 ml of dichloromethane and the mixture was held at 35° C. for 2 hours. The dichloromethane was evaporated under reduced pressure and the residue was extracted with a 1-3 ether-pentane mixture. The extract was filtered and the filtrate was evaporated to dryness. The residue was distilled to obtain diethyl 1-isocyanoethylphosphonate with a boiling point of 82°–84° C. at 0.5 mm Hg.

NMR Spectrum (chloroform):

Peaks at 3.6–4.4 ppm (5H multiplets, hydrogens of methyl and methylene); at 1.2–1.8 ppm (9H multiplet)

STEP C:

20-isocyano-3-methoxy-Δ$^{3,5,17(20)}$-pregnatriene

A solution of 6 g of the product of Step B in 20 ml of dimethoxy methane was added with stirring at 0° to 5° C. over 40 to 50 minutes to a suspension of 6 g of potassium hydride as a 21% oil suspension in 20 ml of dimethoxymethane and 900 mg of 3-methoxy-Δ$^{3,5}$-androstadiene-17-one were added to the mixture. The mixture was held at 0° C. for 4 hours and overnight at room temperature and was then poured into an aqueous saturated sodium chloride solution. The mixture was extracted with ether and the organic phase was washed with water, dried and evaporated to dryness. The residue was chromatographed over alumina and was eluted with a 92-8 hexane-ether mixture to obtain 915 mg (90.5% yield) of 20-isocyano-3-methoxy-Δ$^{3,5,17(20)}$-pregnatriene which melted at 114°~134° C. after crystallization from hexane.

NMR Spectrum (deuterochloroform):

Peaks at 5.20 ppm (1H large 6-hydrogen); at 5.10 ppm (1H large-4-hydrogen); at 3.50 ppm (3H singulet-hydrogens of —OCH$_3$); at 1.85 ppm (3H singulet hydrogens of 21-methyl); at 1.22 ppm (3H singulet-hydrogens of 13-methyl); at 0.98 ppm (3H singulet-hydrogens of 10-methyl).

STEP D:

N-(Δ$^{4,17(20)}$-pregnadiene-3-one-20-yl)-formamide

A solution of 0.5 ml of formic acid and 5 ml of ethyl acetate was added to a solution of 53 mg of the product of Step C in 5 ml of ethyl acetate and the mixture was stirred overnight at room temperature. The ethyl acetate was evaporated without heating under reduced pressure to obtain a solution of N-(Δ$^{4,17(20)}$-pregnadiene-3-one-20-yl)-formamide which was characterized by its spectra.

m/e 341 (M+), 326, 296, 281

IR Spectrum:

Absorptions at 3400, 1660 and 1610 cm$^{-1}$

NMR Spectrum (deuterochloroform):

Peaks at 8.05–8.25 ppm (1H large-hydrogen of formyl); at 6.9–7.4 ppm (1H large-hydrogen on nitrogen); at 5.75 ppm (1H large 4-hydrogen); at 1.85 ppm (3H singulet-hydrogens of 21-methyl); at 1.20 ppm (3H singulet 10-CH$_3$); at 0.95 ppm (3H singulet-13-CH$_3$).

STEP E: (17R) 4'-methylene spiro-[Δ$^4$-androstene-17,5'-(4'H)-oxazol]-3-one 10 ml of dichloromethane were added to the solution of Step D followed by 65 mg of m-chloroperbenzoic acid. After the epoxidation reaction ceased, a few drops of dimethylsulfide and 20 ml of toluene were added to the mixture. The mixture was then heated for about 40 minutes while distilling off about 20 ml of solvent. The resulting solution contained (17R) 4'-methylene spiro-[Δ$^4$-androstene-17,5'-(4'H)-oxazol]-3-one which was characterized by its spectra.

m/e = 339 (M+)

IR Spectrum:
Absorption at 1660 and 1615 $cm^{-1}$

EXAMPLE 3
21-bromo-$\Delta^4$-pregnene-17$\alpha$-ol-3,20-dione

STEP A:
21-bromo-17$\alpha$-formyloxy-$\Delta^4$-pregnene-3,20-dione 0.5 ml of anhydrous pyridine and then a solution of 60 mg of pyridinium perbromide in 6 ml of dichloromethane were added to the cooled anhydrous solution obtained in Example 2 and then 3 ml of acetic acid and 1 ml of water containing 20 to 30 mg of sodium metabisulfite were added thereto. The mixture was heated in a water bath for one hour and was evaporated to dryness under reduced pressure. The residue was taken up in 20 ml of a 2-1 ether-dichloromethane mixture and the solution was washed with water, aqueous sodium bicarbonate solution and dried to obtain an oil which crystallized after trituration with a little methanol. The product was chromatographed over silica gel and was eluted with an ether-dichloromethane mixture to obtain 52 mg of 21-bromo-17$\alpha$-formyloxy-$\Delta^4$-pregnene-3,20-dione melting at 192°–194° C. and having a specific rotation of $[\alpha]_D^{20} = +96°$ (c = chloroform).

STEP B: 21-bromo-$\Delta^4$-pregnene-17$\alpha$-ol-3,20-dione 48 mg of potassium bicarbonate were added to a solution of 43 mg of the product of Step A, 6 ml of methanol and 1 ml of water and the mixture was stirred at room temperature for 3 hours. 5 drops of acetic acid and 10 ml of dilute sodium chloride solution were added to the mixture which was then extracted with methylene chloride. The organic phase was dried and evaporated to dryness to obtain 21-bromo-$\Delta^4$-pregnene-17$\alpha$-ol-3,20-dione conforming to the product described in the literature.

Various modifications of the products and products of the invention may be made without departing from the spirit or scope thereof and it is to be understood that the invention is intended to be limited only as defined in the appended claims.

What we claim is:

1. A compound having a formula selected from the group consisting of

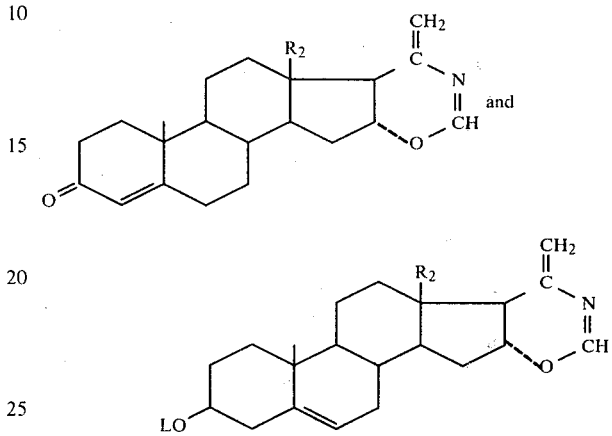

wherein $R_2$ is alkyl of 1 to 4 carbon atoms and L is selected from the group consisting of methoxymethyl, $\beta$-methoxyethoxymethyl, benzyl, p-nitrobenzyl, trimethylsilyl, tert.-butyldimethylsilyl, triethylsilyl, acetyl, propionyl and benzoyl.

2. The compound of claim 1 wherein $R_2$ is methyl.

3. A compound of claim 1 which is (17R) 4'-methylene spiro-[$\Delta^4$-androsten-17,5'-(4'H)-oxazol]-3-one.

4. A compound of claim 1 which is (17R) 3$\beta$-acetyloxy-2'-methyl-4'-methylene spiro [$\Delta^5$-androsten-17,5'-(4'H)-oxazole].

* * * * *

UNITED STATES PATENT AND TRADEMARK OFFICE
CERTIFICATE OF CORRECTION

PATENT NO. : 4,401,596  Page 1 of 2
DATED : Aug. 30, 1983
INVENTOR(S) : DEREK H. BARTON, WILLIAM B. MOTHERWELL, SAMIR ZARD ZARD It is certified that error appears in the above-identified patent and that said Letters Patent is hereby corrected as shown below:

Under the Abstract

"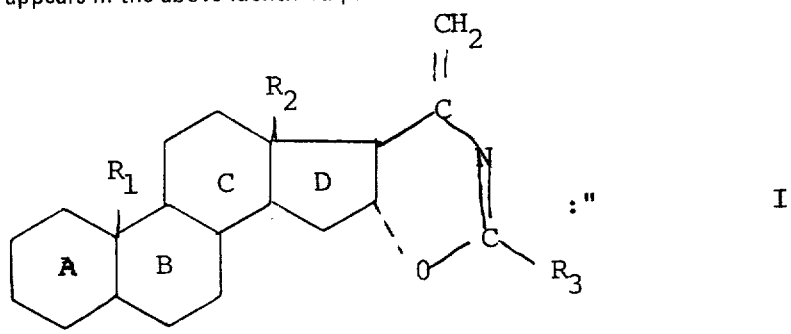 :"   I should be

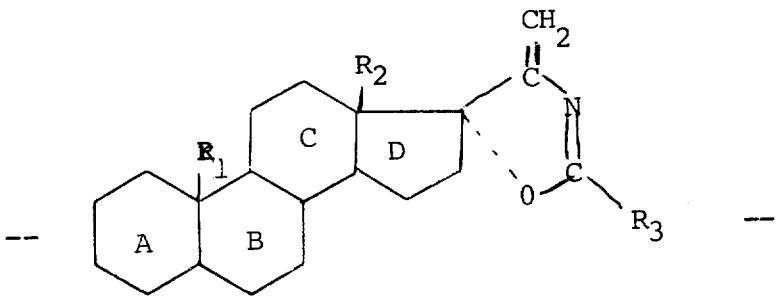

--            --

In Col. 1   same as above

UNITED STATES PATENT AND TRADEMARK OFFICE
CERTIFICATE OF CORRECTION

PATENT NO. : 4,401,596

DATED : Aug. 30, 1983

INVENTOR(S) : DEREK H. BARTON, WILLIAM B. MOTHERWELL, SAMIR ZARD ZARD

It is certified that error appears in the above-identified patent and that said Letters Patent is hereby corrected as shown below:

In Col. 8 Claim 1 The 2 formulae

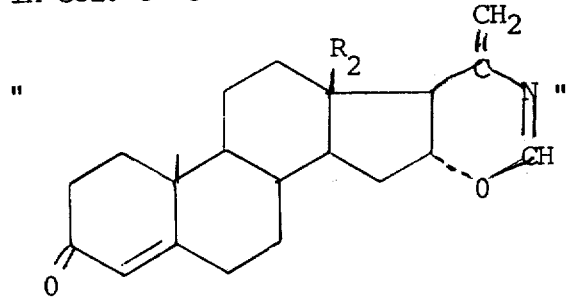

and

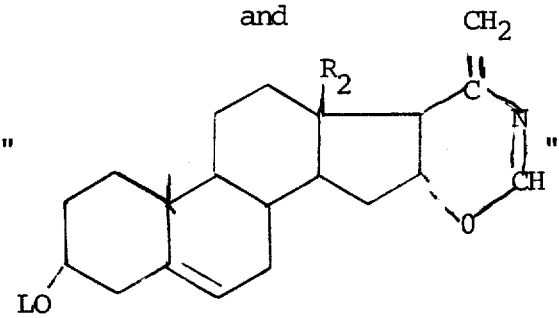

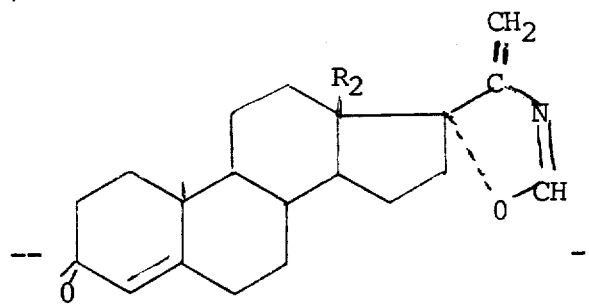

--

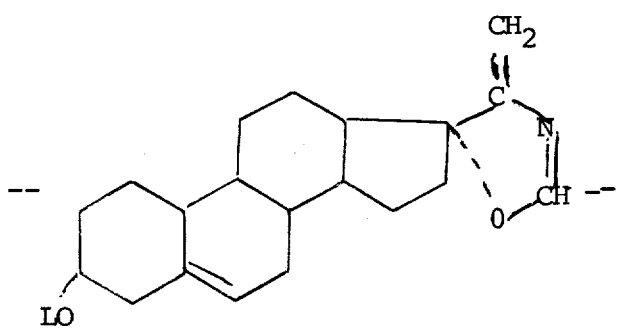

--

Signed and Sealed this

Twenty-first Day of May 1985

[SEAL]

Attest:

DONALD J. QUIGG

Attesting Officer

Acting Commissioner of Patents and Trademarks